United States Patent

Knoesche et al.

(10) Patent No.: US 8,288,584 B2
(45) Date of Patent: Oct. 16, 2012

(54) PROCESS FOR PREPARING ISOCYANATES

(75) Inventors: Carsten Knoesche, Niederkirchen (DE); Andreas Woelfert, Bad Rappenau (DE); Torsten Mattke, Freinsheim (DE); Eckhard Stroefer, Mannheim (DE); Heinrich-Josef Blankertz, Forst (DE); Bernhard Geissler, Kirchheim (DE)

(73) Assignee: BASF SE, Ludwigshafen (DE)

( * ) Notice: Subject to any disclaimer, the term of this patent is extended or adjusted under 35 U.S.C. 154(b) by 371 days.

(21) Appl. No.: 12/678,771

(22) PCT Filed: Sep. 11, 2008

(86) PCT No.: PCT/EP2008/062038
§ 371 (c)(1), (2), (4) Date: Mar. 18, 2010

(87) PCT Pub. No.: WO2009/037179
PCT Pub. Date: Mar. 26, 2009

(65) Prior Publication Data
US 2010/0217035 A1    Aug. 26, 2010

(30) Foreign Application Priority Data

Sep. 19, 2007   (EP) .................................. 07116729

(51) Int. Cl.
*C07C 263/10* (2006.01)
(52) U.S. Cl. ........................... 560/341; 560/347
(58) Field of Classification Search .................. None
See application file for complete search history.

(56) References Cited

U.S. PATENT DOCUMENTS

| 5,449,818 | A | 9/1995 | Biskup et al. |
| 2008/0027242 | A1 | 1/2008 | Knosche et al. |
| 2008/0200722 | A1 | 8/2008 | Wolfert et al. |
| 2009/0281350 | A1 | 11/2009 | Knoesche et al. |
| 2010/0041914 | A1 | 2/2010 | Woelfert et al. |
| 2010/0041915 | A1 | 2/2010 | Woelfert et al. |
| 2010/0048942 | A1 | 2/2010 | Knoesche et al. |
| 2010/0056822 | A1 | 3/2010 | Daiss et al. |

FOREIGN PATENT DOCUMENTS

| DE | 102 60 092 | 7/2004 |
| EP | 0 289 840 | 11/1988 |
| EP | 0 570 799 | 11/1993 |
| EP | 0 593 334 | 4/1994 |
| EP | 0 699 657 | 3/1996 |
| EP | 0 749 958 | 12/1996 |
| EP | 1 078 918 | 2/2001 |
| EP | 1 275 639 | 1/2003 |
| EP | 1 275 640 | 1/2003 |
| EP | 1 319 655 | 6/2003 |
| EP | 1 362 847 | 11/2003 |
| EP | 1 403 248 | 3/2004 |
| EP | 1 449 826 | 8/2004 |
| WO | 03 045900 | 6/2003 |
| WO | 2004 014845 | 2/2004 |
| WO | 2004 026813 | 4/2004 |
| WO | 2004 037718 | 5/2004 |
| WO | 2005 123665 | 12/2005 |
| WO | 2007 014936 | 2/2007 |
| WO | 2008 006775 | 1/2008 |
| WO | 2008 055899 | 5/2008 |
| WO | 2008 055904 | 5/2008 |

OTHER PUBLICATIONS

U.S. Appl. No. 13/001,681, filed Dec. 28, 2010, Knoesche, et al.
U.S. Appl. No. 13/266,049, filed Oct. 24, 2011, Stroefer, et al.
U.S. Appl. No. 12/446,460, filed Apr. 21, 2009, Boehling, et al.
U.S. Appl. No. 12/447,940, filed Apr. 30, 2009, Daiss, et al.
U.S. Appl. No. 12/675,187, filed Feb. 25, 2010, Olbert, et al.
U.S. Appl. No. 12/675,137, filed Feb. 25, 2010, Olbert, et al.
U.S. Appl. No. 12/675,095, filed Feb. 24, 2010, Rumpf, et al.
U.S. Appl. No. 13/380,357, filed Dec. 22, 2011, Schelling, et al.
U.S. Appl. No. 13/380,680, filed Dec. 23, 2011, Schelling, et al.
U.S. Appl. No. 13/383,549, filed Jan. 11, 2012, Schelling, et al.
U.S. Appl. No. 13/383,433, filed Jan. 11, 2012, Schelling, et al.

*Primary Examiner* — Kamal Saeed
(74) *Attorney, Agent, or Firm* — Oblon, Spivak, McClelland, Maier & Neustadt, L.L.P.

(57) ABSTRACT

The present invention relates to a process for preparing diisocyanates from diamines and phosgene in the gas phase.

13 Claims, 3 Drawing Sheets

PROCESS FOR PREPARING ISOCYANATES

BACKGROUND OF THE INVENTION

The present invention relates to a process for preparing diisocyanates from diamines and phosgene in the gas phase.

The phosgenation of amines to isocyanates in the gas phase is known, for example—in addition to numerous other documents—from EP 570799, EP 749 958 B1 and EP 1078918 B1.

In the known gas phase phosgenation processes, phosgene is evaporated before use in the process. This entails storage of liquid phosgene as a reservoir for use in the process and the supply of energy for evaporation.

Owing to the high toxicity of the phosgene, the aim for safety reasons is to keep the reservoir of phosgene and the amount of phosgene which are each present in the process stages (holdup) as low as possible. This aim is countered by the superstoichiometric use of the phosgene in the conversion of amine, such that considerable amounts of phosgene have to be recycled owing to the reaction.

It was an object of the present invention to provide a process for preparing diisocyanates, with which the amount of phosgene in the individual process stages of the diisocyanate preparation can be reduced.

BRIEF SUMMARY OF THE INVENTION

The object was achieved by a process for preparing diisocyanates by reacting the corresponding diamines with phosgene in a stoichiometric excess of phosgene in at least one reaction zone, comprising at least the process stages of:
  mixing (V) at least one stream comprising gaseous phosgene with at least one stream comprising gaseous diamine, and converting this mixture at a temperature of from 200 to 600° C. in the at least one reaction zone (VI),
  mixing (VII) the resulting reaction mixture, which consists essentially of isocyanate, phosgene and hydrogen chloride, with at least one liquid while lowering the temperature to from 100 to 200° C., such that the isocyanate present in the reaction mixture is transferred at least partly to the liquid by condensation, while phosgene and hydrogen chloride remain essentially completely in the gas phase (quench),
  (VIII) working up the condensed isocyanate with evaporation of the phosgene and hydrogen chloride remaining in the condensed phase,
  (IX) separating the combined gaseous streams comprising essentially hydrogen chloride and phosgene into a stream comprising predominantly phosgene and a stream comprising predominantly hydrogen chloride,
  recycling the thus obtained stream comprising predominantly phosgene into the mixing (V),
in which the phosgene present in the process stages is present essentially in gaseous form.

In the gas phase phosgenation, the aim in accordance with the invention is that all compounds which occur in the course of the reaction, i.e. reactants (diamine and phosgene), intermediates (especially the mono- and dicarbamoyl chlorides formed as intermediates), end products (diisocyanate, hydrogen chloride), and any inert medium metered in remain in the gas phase under the reaction conditions.

Should these or other components separate out of the gas phase, for example at the reactor wall or other apparatus components, the heat transfer or the flow through the components in question may be changed undesirably as a result of these depositions.

DETAILED DESCRIPTION OF THE INVENTION

Figure 1:
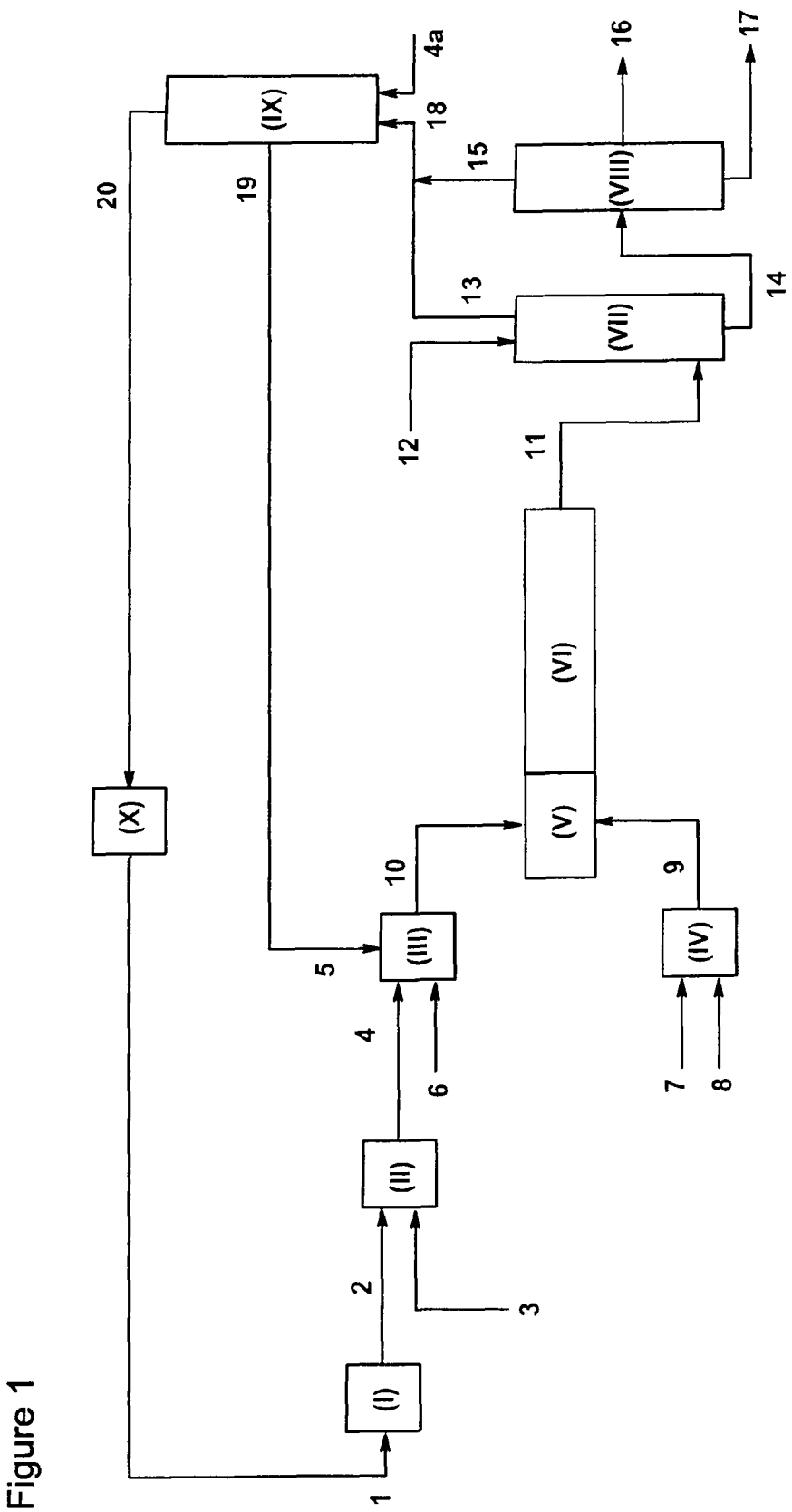
FIG. 1. A schematic diagram of a preferred embodiment of the process according to the present invention.

In the process according to the invention, phosgene is reacted with diamine in the gas phase. Reaction in the gas phase is understood to mean that the reactant streams react with one another in the gaseous state.

Diisocyanates which can be prepared by the process according to the invention may be aromatic, cycloaliphatic or aliphatic.

Cycloaliphatic isocyanates are those which comprise at least one cycloaliphatic ring system.

Aliphatic isocyanates are those which have exclusively isocyanate groups which are bonded to straight or branched chains. These may also comprise aromatic ring systems, provided that no isocyanate groups are bonded to them.

Aromatic isocyanates are those which have at least one isocyanate group bonded to at least one aromatic ring system.

In the context of this application, (cyclo)aliphatic isocyanates are an abbreviated representation of cycloaliphatic and/or aliphatic isocyanates.

Examples of aromatic diisocyanates are preferably those having 6-20 carbon atoms, for example monomeric methylene di(phenyl isocyanate) (MDI), tolylene 2,4- and/or 2,6-diisocyanate (TDI) and naphthyl diisocyanate (NDI).

Diisocyanates are preferably (cyclo)aliphatic diisocyanates, more preferably (cyclo)aliphatic diisocyanates having from 4 to 20 carbon atoms.

Examples of customary diisocyanates are aliphatic diisocyanates such as tetramethylene diisocyanate, pentamethylene diisocyanate (1,5-diisocyanatopentane), hexamethylene diisocyanate (1,6-diisocyanatohexane), 2-methylpentane 1,5-diisocyanate, octamethylene 1,8-diisocyanate, decamethylene 1,10-diisocyanate, dodecamethylene 1,12-diisocyanate, tetradecamethylene 1,14-diisocyanate, derivatives of lysine diisocyanate, tetramethylxylylene diisocyanate (TMXDI), trimethylhexane diisocyanate or tetramethylhexane diisocyanate, and also 3 (or 4),8 (or 9)-bis(isocyanatomethyl)-tricyclo[5.2.1.0$^{2,6}$]decane isomer mixtures, and also cycloaliphatic diisocyanates such as 1,4-, 1,3- or 1,2-diisocyanatocyclohexane, 4,4'- or 2,4'-di(isocyanatocyclo-hexyl)methane, 1-isocyanato-3,3,5-trimethyl-5-(isocyanatomethyl)cyclohexane (isophorone diisocyanate), 1,3- or 1,4-bis(isocyanatomethyl)cyclohexane, 2,4- or 2,6-diisocyanato-1-methylcyclohexane.

Preference is given to 1,6-diisocyanatohexane, 1-isocyanato-3,3,5-trimethyl-5-(isocyanatomethyl)cyclohexane, 4,4'-di(isocyanatocyclohexyl)methane and tolylene diisocyanate isomer mixtures. Particular preference is given to 1,6-diisocyanatohexane, 1-isocyanato-3,3,5-trimethyl-5-(isocyanatomethyl)cyclohexane and 4,4'-di(isocyanatocyclohexyl)methane.

Apart from diisocyanates, it is in principle also possible by the process according to the invention monoisocyanates having one isocyanate group or higher isocyanates having an average of more than 2 isocyanate groups. Suitable examples include triisocyanates such as triisocyanatononane, 2,4,6-triisocyanatotoluene, triphenylmethane triisocyanate or 2,4,4'-triisocyanatodiphenyl ether, or the mixtures of diisocyanates, triisocyanates and higher polyisocyanates which are obtained, for example, by phosgenation of corresponding aniline/formaldehyde condensates and are polyphenyl polyisocyanates having methylene bridges.

A preferred monoisocyanate is phenyl isocyanate.

Preference is given, however, to the preparation of diisocyanates.

For the process according to the invention, it is possible to use those amines for the reaction to give the corresponding diisocyanates which can be converted to the gas phase preferably without significant decomposition, i.e. undecomposed to an extent of at least 95% by weight, preferably to an extent of at least 98% by weight, more preferably to an extent of at least 99% by weight, even more preferably to an extent of at least 99.5% by weight, in particular to an extent of at least 99.8% by weight, especially to an extent of at least 99.9% by weight and even to an extent of at least 99.95% by weight. Particularly suitable here are amines, especially diamines, based on aliphatic or cycloaliphatic hydrocarbons having from 2 to 18 carbon atoms. Examples thereof are 1,6-diaminohexane, 1-amino-3,3,5-trimethyl-5-aminomethylcyclohexane (IPDA) and 4,4'-diaminodicyclohexylmethane. Preference is given to using 1,6-diaminohexane (HDA).

For the process according to the invention, it is likewise possible to use aromatic amines which can be converted to the gas phase preferably without significant decomposition. Examples of preferred aromatic amines are tolylenediamine (TDA), as the 2,4- or 2,6-isomer or as a mixture thereof, diaminobenzene, R,S-1-phenylethylamine, 1-methyl-3-phenylpropylamine, 2,6-xylidine, 3,3'-diaminodiphenyl sulfone, napthyldiamine (NDA) and 2,4'- or 4,4'-methylene(diphenylamine) (MDA) or isomer mixtures thereof. Among these, preference is given to the diamines, particular preference to 2,4- and/or 2,6-TDA.

The reactants, or else only one of them, may, as appropriate individually or in each case together with an inert medium, be metered into the reaction chamber.

In the process according to the invention, an additional inert medium may be added to the phosgene stream and/or amine stream. The inert medium is a medium which is present in gaseous form in the reaction chamber at the reaction temperature and essentially does not react with the compounds which occur in the course of the reaction or is stable under the reaction conditions. Preference is given to those inert media which remain undecomposed and unreacted to an extent of at least 95% by weight under the reaction conditions, preferably to an extent of at least 98% by weight, more preferably to an extent of at least 99% by weight, even more preferably to an extent of at least 99.5% by weight, in particular to an extent of at least 99.8% by weight, especially to an extent of at least 99.9% by weight and even to an extent of at least 99.95% by weight. The inert medium is generally mixed with amine and/or phosgene before the reaction, but may also, for example, be metered directly into the reaction zone separately from the reactant streams. For example, it is possible to use nitrogen, carbon dioxide or carbon monoxide, noble gases such as helium or argon, or aromatics such as toluene or xylene, or chlorinated aromatics such as chlorobenzene or dichlorobenzene. Preference is given to using nitrogen and/or chlorobenzene as the inert medium.

In general, the inert medium is used in an amount such that the ratio of the gas volumes of inert medium to amine or to phosgene is from more than 0.0001 to 30, preferably from more than 0.001 to 15, more preferably from more than 0.001 to 5.

Preference is given to introducing the inert medium into the reaction chamber together with the diamine. However, other means of metered addition are also conceivable.

The phosgene can also be supplied to the reaction chamber via the phosgene-containing stream in such a way that several phosgene-containing substreams are supplied instead of one individual phosgene-containing stream. In such a case, the phosgene-containing substreams are added to give an overall phosgene-containing overall stream.

Such substreams can be metered in in the following manner:

Different phosgene-containing substreams, for example recycled phosgene and fresh phosgene, can be combined to a phosgene-containing overall stream before being fed in, and can be fed into the reaction chamber.

Several substreams, which may each be recycled phosgene, fresh phosgene or mixtures thereof, can be fed into the reaction chamber at the same point. This can be done, for example, via several nozzles which are arranged in parallel around a central nozzle, as described, for example, in EP 1449826 A1, or by multiple spraying into a ring space for mixing, before this stream is mixed with an amine-containing stream metered in via a central nozzle.

Several substreams, which may in each case be recycled phosgene, fresh phosgene or mixtures thereof, can be metered in at different points in the reaction chamber, such that phosgene is replenished in the course of the reaction.

The term "fresh phosgene" refers to a phosgene-containing stream which has not been recycled from a phosgenation process, but which, after the synthesis of the phosgene, usually from chlorine and carbon monoxide, has not passed through a reaction stage with a phosgene conversion in which more than 5% conversion of the phosgene prepared in the phosgene synthesis proceeds.

In a preferred embodiment of the present invention, the fresh phosgene, after its synthesis and optional purification in a plant for preparing phosgene (II), is conducted into the process according to the invention essentially in gaseous form. For this purpose, the process according to the invention is preferably connected directly, more preferably via a pipeline, to a plant for preparing phosgene.

This has the consequence that, firstly, in accordance with the invention, it is possible to dispense with the supply of energy to evaporate liquid phosgene, and, secondly, the reservoir of phosgene is limited to the gaseous phosgene present in this pipeline.

Frequently, phosgene is prepared by contacting carbon monoxide with molecular chlorine ($Cl_2$) over suitable supports, preferably activated carbon. Since the formation of phosgene is strongly exothermic, this is preferably done in tube bundle reactors, in which the support bed is heated by the exothermic reaction to temperatures up to 400° C., although the temperature falls to from 40 to 150° C. as it passes through the tube. The heat of reaction released is removed by suitable heat carrier media, for example monochlorobenzene, dichlorobenzene or water. Also conceivable are heat carrier oils. Usually, standard pressure or slightly elevated pressure is present.

The phosgene obtained in gaseous form to an extent, for example, of at least 75% by weight in gaseous form, preferably to an extent of at least 85% by weight, more preferably to an extent of at least 90% by weight, even more preferably to an extent of at least 95% by weight, in particular to an extent of at least 98% by weight, especially to an extent of at least 99% by weight and even to an extent of at least 99.5% by weight can preferably be used in the gas phase phosgenation without further purification and especially without intermediate condensation. If desired, it is possible, for example, by means of scrubbing to remove by-products from the reaction mixture by absorption.

However, it may also be advisable to use the amine used in the form of an aerosol, i.e. essentially as a finely distributed liquid having a droplet size distribution of from 10 nm to 1 mm, preferably from 100 nm to 100 μm, especially from 0.2 to 10 μm. The droplet size distribution may be very wide or very narrow between these limits. In the ideal case, the droplet size distribution is very narrow. A measure used for the width of the distribution is the standard deviation a normalized to the $d_{50}$ of the droplet size distribution. The $d_{50}$ is the droplet size for which the cumulative distribution function reaches the value of 0.5 (50%). For a very wide distribution, σ>>1. For a narrow distribution, σ<1, and, for an ideally monodisperse distribution, the value σ=0.

In general, the size of the droplets should be as small as possible, since this ensures a high penetration rate of the phosgene into the liquid amine-containing phase. In addition, the realizable droplet diameter restricts the maximum size of the amine hydrochloride particles which precipitate out. It is therefore the case here too that a fine aerosol is preferable over a very coarse aerosol. However, it must be ensured that the aerosol/product obtained is also separated out by the downstream droplet/dust separators.

Such a process is described, for example, in the international patent application WO 2008/006775, which is hereby fully incorporated by reference.

In a preferred embodiment of the present invention, phosgene is prepared with a stoichiometric excess of carbon monoxide, in which case complete conversion of the chlorine is generally achieved. The phosgene obtained in this way still comprises small amounts, generally not more than 5% by weight, of carbon monoxide. However, this has no adverse effect on the use in the process according to the invention, since the carbon monoxide present functions as an inert gas in the gas phase phosgenation. The carbon monoxide present is then generally discharged in the hydrogen chloride removal (IX) (see below).

In a preferred embodiment, the phosgene is not conducted directly into the synthesis but rather first into the phosgene purification in stage (IX) (see below).

This embodiment is represented by stream 4a in FIG. 1.

This may be advisable especially in order to remove traces of molecular chlorine, such that this embodiment is especially preferred when the phosgene obtained from the phosgene synthesis still comprises traces of molecular chlorine ($Cl_2$), for example at a content of more than 5 ppm, preferably at more than 3 ppm, more preferably at more than 1 ppm, even more preferably at more than 0.5 ppm and especially at a content of more than 0.1 ppm.

To perform the process according to the invention, it may be advantageous to preheat the streams of the amine and/or phosgene reactants before mixing, preferably to superheat them, for example to temperatures of at least 200° C., preferably at least 260° C. and more preferably at least 300° C.

In the amine reservoir (IV), the amine is preferably converted to the gas phase as described above together with an inert medium as the carrier gas, and fed into the mixing unit (V). However, the amine can also be evaporated directly without use of an inert medium and be conducted into the mixing unit (V).

The gaseous phosgene stream comprising fresh and recycled phosgene is superheated to the temperature mentioned. If appropriate, it can be mixed with at least one inert medium and then fed to the mixing unit (V).

In the process according to the invention, the reactants are mixed in a mixing device (V), which is notable for a high shear of the reaction streams conducted through the mixing device. Preference is given to using, as the mixing device, a static mixing device or a mixing nozzle which is positioned upstream of the reaction zone (VI). Particular preference is given to using a mixing nozzle.

The type of mixing is of no importance in accordance with the invention and it can be done in any desired manner, for example as described in EP-B1 699657, EP-A2 1319655, column 1 line 54 to column 2, line 24 and column 4, lines 16-40, EP-A1 1275640, column 3 line 27-column 4 line 5, EP-A2 1362847, column 2 line 19-column 3 line 51 and column 4 line 40-column 5 line 12, each of which is explicitly incorporated in the context of this disclosure.

In the process, phosgene is typically used in excess based on amino groups. Typically, a molar ratio of phosgene to amino groups of from 1.1:1 to 20:1, preferably from 1.2:1 to 5:1, is present.

After the mixing in the mixing unit (V), the gaseous mixture of phosgene, amine and, if appropriate, inert medium is conducted into the reactor, the reactor comprising the reaction chamber.

The reaction of phosgene with amine proceeds in a reaction chamber which is generally arranged in a reactor, i.e. reaction chamber (VI) is understood to mean the chamber in which a part of the conversion of the reactants and intermediates and/or of the products which is relevant for the yield of the process is carried out and in which, for example, at least 0.5 mol % of the amine used is consumed and/or of the corresponding isocyanate is formed, preferably at least 1 mol %, more preferably at least 3 mol %, even more preferably at least 5 mol %, in particular at least 7 mol % and especially at least 10 mol % of the amine used is consumed and/or of the corresponding isocyanate is formed.

Reactor is understood to mean the technical apparatus which comprises the reaction chamber. It may be all customary reaction chambers known from the prior art which are suitable for the noncatalytic, monophasic gas reaction, preferably for the continuous noncatalytic, monophasic gas reaction, and which withstand the pressures required. Suitable materials for the contact with the reaction mixture are, for example, metals such as steel, especially alloyed steel, tantalum, nickel, nickel alloys, silver or copper, glass, ceramic, enamel or homogeneous or heterogeneous mixtures and components thereof. Preference is given to using steel reactors. The walls of the reactor may be smooth or profiled. Suitable profiles are, for example, cracks or waves.

It is generally possible to use the reactor designs known from the prior art. Examples of reactors are known from EP-B1 289840, column 3 line 49-column 4 line 25, EP-B1 593334, WO 2004/026813, page 3 line 24-page 6 line 10, WO 03/045900, page 3 line 34-page 6 line 15, EP-A1 1275639, column 4 line 17-column 5 line 17, and EP-B1 570799, column 2 line 1-column 3 line 42, each of which is incorporated explicitly in the scope of this disclosure by reference.

Preference is given to using tubular reactors.

It is likewise possible to use essentially cuboidal reaction chambers, preferably plate reactors or plate reaction chambers. A particularly preferred plate reactor has a ratio of width to height of at least 2:1, preferably at least 3:1, more preferably at least 5:1 and especially at least 10:1. The upper limit in the ratio of width to height depends upon the desired capacity of the reaction chamber and is in principle not limited. Technically viable reaction chambers have been found to be those with a ratio of width to height up to at most 5000:1, preferably 1000:1.

The reaction of phosgene with amine in the reaction chamber (VI) is effected at absolute pressures of from more than 0.1 bar to less than 20 bar, preferably between 0.5 bar and 10 bar, more preferably between 0.7 bar and 5 bar, in particular from 0.8 to 3 bar.

In general, the pressure in the feed lines to the mixing apparatus is higher than the above-specified pressure in the reactor. According to the selection of the mixing apparatus, at this pressure declines. The pressure in the feed lines is preferably higher by from 20 to 10 000 mbar, more preferably from 30 to 7000 mbar, than in the reaction chamber.

In a preferred embodiment, the reactor consists of a bundle of reactors. In one possible embodiment, the mixing unit need not be an independent apparatus; instead, it may be advantageous to integrate the mixing unit into the reactor. One example of an integrated unit composed of mixing unit and reactor is that of a tubular reactor with flanged-on nozzles.

In general, the pressure in the workup apparatus is lower than in the reaction chamber.

In the process according to the invention, the reaction of phosgene with amine is effected in the gas phase. Reaction in the gas phase is understood to mean that the conversion of the reactant streams and intermediates to the products react with one another in the gaseous state and, in the course of the reaction during passage through the reaction chamber, remain in the gas phase to an extent of at least 95%, preferably to an extent of at least 98%, more preferably to an extent of at least 99%, even more preferably to an extent of at least 99.5%, in particular to an extent of at least 99.8% and especially to an extent of at least 99.9%.

Intermediates are, for example, the monoamino monocarbamoyl chlorides, dicarbamoyl chlorides, monoamino monoisocyanates and monoisocyanato monocarbamoyl chlorides formed from the diamines, and also the hydrochlorides of the amino compounds.

In the process according to the invention, the temperature in the reaction chamber (VI) is selected such that it is above the dissociation temperature of the hydrochlorides of the diamine used, based on the partial pressure conditions existing in the reaction chamber. According to the amine used and pressure established, an advantageous temperature in the reaction chamber of more than 200° C., preferably more than 260° C. and more preferably more than 300° C. typically arises. In general, the temperature is up to 600° C., preferably up to 570° C.

The mean contact time of the reaction mixture in the process according to the invention is generally between 0.001 second and less than 5 seconds, preferably from more than 0.01 second to less than 3 seconds, more preferably from more than 0.02 second to less than 1.5 seconds. Mean contact time is understood to mean the time lapse from the beginning of mixing of the reactants until they leave the reaction chamber into the workup stage. In a preferred embodiment, the flow in the process according to the invention is characterized by a Bodenstein number of more than 10, preferably more than 100 and more preferably of more than 500.

In a preferred embodiment, the dimensions of the reaction chamber and the flow rates are selected such that a turbulent flow is present for the reaction mixture, i.e. a flow with a Reynolds number of at least 2300, preferably at least 2700, the Reynolds number being formed with the hydraulic diameter of the reaction chamber.

The gaseous reactants preferably flow through the reaction chamber with a flow rate of from 3 to 400 meters/second, preferably from 10 to 250 meters/second. As a result of the turbulent flow, a narrow residence time with a low standard deviation of usually not more than 6%, as described in EP 570799, and good mixing are achieved. Measures, for example the constriction described in EP-A-593 334, which is additionally prone to blockage, are not necessary.

The reaction volume may be temperature-controlled over its outer surface. In order to build production plants with a high plant capacity, it is possible to connect a plurality of reactor tubes in parallel. However, the reaction can also be effected adiabatically. This means that heating or cooling energy streams do not flow over the outer surface of the reaction volume by technical measures. The reaction preferably takes place adiabatically.

The phosgenation process is preferably carried out in one stage. This is understood to mean that the mixing (V) and conversion (VI) of the reactants are effected in one stage and within one temperature range, preferably within the aforementioned temperature range. Moreover, the process according to the invention is preferably carried out continuously.

After the reaction, the reaction mixture is fed to a mixing device VII (quench), in which the temperature of the gas is lowered by introducing a cooler liquid. Embodiments of this process stage may be: scrubbing towers, stirred vessels, bubble columns, quench nozzles and the like. In these, contact with at least one, preferably exactly one, inert solvent causes the isocyanate formed to be condensed out of the gaseous reaction mixture, while excess phosgene, hydrogen chloride and if appropriate the inert medium pass through this workup apparatus essentially in gaseous form.

Suitable inert solvents are preferably hydrocarbons which are optionally substituted by halogen atoms, for example chlorobenzene, dichlorobenzene, 1,3,5-trimethylbenzene (mesitylene), xylene and toluene. Preference is given to keeping the temperature of the inert solvent above the melting point of the carbamyl chloride corresponding to the amine. Particular preference is given to keeping the temperature of the inert solvent above the dissolution temperature of the carbamyl chloride corresponding to the amine in the selected quench medium.

For this process stage in the process according to the invention, it is possible, in terms of process technology, to use all extraction processes and apparatus and scrubbing processes and apparatus known per se, for example those described in Ullmann's Encyclopedia of Industrial Chemistry, 6th ed, 1999 Electronic Release, chapter: Liquid —Liquid Extraction—Apparatus. For example, these may be single-stage or multistage, preferably single-stage, extractions, and also those in cocurrent or countercurrent mode, preferably countercurrent mode.

A further suitable quench is known, for example, from EP-A1 1403248, column 2 line 39-column 3 line 18, which is explicitly incorporated in the context of this disclosure. In addition, the quench may also be designed as described in WO 2008/055899 and WO 2008/055904 or as in the international application WO 2005/123665.

In process stage (VII), the reaction mixture, which consists essentially of the isocyanates, phosgene and hydrogen chloride, is mixed intensively with the liquid sprayed in. The mixing is effected by lowering the temperature of the reaction mixture, proceeding from 200 to 570° C., to 100 to 200° C., preferably to 100 to 180° C., and the isocyanate present in the reaction mixture is transferred by condensation fully or partly to the liquid droplets sprayed in, while the phosgene and the hydrogen chloride remain essentially completely in the gas phase.

The proportion of the isocyanate which is present in the gaseous reaction mixture and is transferred to the liquid phase in the quench zone is preferably from 20 to 100% by weight, more preferably from 50 to 99.5% by weight and especially from 70 to 99% by weight, based on all of the isocyanate present in the reaction mixture.

The proportion of the phosgene and hydrogen chloride which is present in the gaseous reaction mixture and is transferred to the liquid phase in the quench zone is generally less than 25% by weight.

In the reaction mixture, the conversion of amino groups should be at least 95%, preferably at least 98%, more preferably at least 99%, even more preferably at least 99.5%, in particular at least 99.8% and especially at least 99.9%.

The reaction mixture flows through the quench zone preferably from the top downward. Below the quench zone is arranged a collecting vessel in which the liquid phase is separated out, collected, removed through an outlet and then worked up. The remaining gas phase is removed from the collecting vessel via a second outlet and likewise worked up.

The quench liquid must have a good solubility for isocyanates. Preference is given to using organic solvents. In particular, aromatic solvents which may be substituted by halogen atoms are used. Examples of such liquids are toluene, benzene, nitrobenzene, anisole, chlorobenzene, dichlorobenzene (ortho or para or isomer mixtures thereof), trichlorobenzene, 1,3,5-trimethylbenzene (mesitylene), xylene, hexane, diethyl isophthalate (DEIP), tetrahydrofuran (THF), dimethylformamide (DMF) and mixtures thereof, preferably monochlorobenzene.

In a particular embodiment of the process according to the invention, the liquid sprayed in is a mixture of isocyanates, a mixture of isocyanates and solvent, or isocyanate, and the quench liquid used in each case may comprise fractions of low boilers, such as hydrogen chloride and phosgene. Preference is given to using the isocyanate which is prepared in the particular process. Since the lowering of the temperature in the quench zone brings the reaction to a standstill, side reactions with the isocyanates sprayed in can be ruled out. The advantage of this embodiment is especially that a removal of the solvent can be dispensed with.

In an alternative preferred embodiment, the inert medium which is used together with at least one of the reactants and the solvent which is used in the quench are the same compound; most preferably, monochlorobenzene is used in this case.

The quench liquid discharged from stage (VII) may, as well as diisocyanate, also comprise up to 10% by weight of phosgene and/or up to 10% by weight of hydrogen chloride.

In order to keep the absorption of phosgene in the quench liquid low in accordance with the invention, the quench is preferably performed at low pressure, for example from 1 to 5 bar, and elevated temperature, for example from 100 to 160° C.

Small amounts of by-products which remain in the isocyanate can be separated from the desired isocyanate by means of additional rectification, by stripping with an inert gas, or else crystallization, preferably by rectification.

In the subsequent optional purification stage (VIII), the isocyanate is removed from the solvent, preferably by distillation or more preferably by rectification. It is likewise possible here to remove residual impurities comprising hydrogen chloride, inert medium and/or phosgene, as described, for example, in DE-A1 10260092.

Gaseous streams which consist essentially of phosgene and/or hydrogen chloride gas and/or inert medium are obtained from the quench (VII) and/or the purification stage (VIII). Hydrogen chloride is removed from the phosgene in stage (IX) in at least some of these streams comprising phosgene and/or hydrogen chloride gas and/or inert medium.

This can be done, for example, as described in international application WO 2007/014936. In a scrubbing, hydrogen chloride is absorbed from the gas mixture in a suitable scrubbing liquid. The remaining phosgene leaves the column in gaseous form and can be recycled into the reaction. Suitable scrubbing liquids described in WO 2007/014936 are ionic liquids. This process variant is particularly advantageous, since it avoids phosgene in condensed phase.

In a further preferred embodiment, the removal is effected such that the mass fraction of hydrogen chloride in the phosgene-containing stream, after optional mixing with fresh phosgene before the mixing with the amine-containing stream, is less than 15% by weight, preferably less than 10% by weight, more preferably less than 5% by weight.

The separation of the hydrogen chloride and/or phosgene and mixture possibly comprising solvent from the quench is preferably effected by means of distillation and/or a scrubbing. Preference is given to carrying out the separation in a combination of a distillation and a scrubbing.

Preferred scrubbing media for the phosgene-hydrogen chloride separation (IX) are the solvents listed above as quench media. Particular preference is given to using the same solvents as the scrubbing medium and as the quench medium in stages (VII) and (IX).

In the case of a combined scrubbing and distillation, for example a pressure distillation, phosgene is scrubbed out of the hydrogen chloride-containing stream by scrubbing with a scrubbing medium, preferably toluene, chlorobenzene or dichlorobenzene. As an exception, phosgene is present here in condensed form in the process according to the invention. Phosgene and hydrogen chloride are removed from the laden scrubbing medium after the scrubbing preferably by distillation or by desorption. The removal is preferably effected so as to obtain a gaseous phosgene stream which, in a particularly preferred embodiment, if appropriate after mixing with fresh phosgene, comprises a content of hydrogen chloride of less than 15% by weight.

The scrubbing and the distillation are conducted at pressures of from 1 to 10 bar absolute, preferably from 1 to 5 bar absolute.

The hydrogen chloride/phosgene separation (IX) may be followed downstream by an adsorption unit, preferably an activated carbon filter, in the hydrogen chloride stream removed from the separation, in which traces of the scrubbing medium are removed from the hydrogen chloride obtained.

A preferred embodiment of the process according to the invention is shown schematically in FIG. 1.

In FIG. 1:
I preparation unit for chlorine ($Cl_2$)
II preparation unit for phosgene
III mixing of phosgene and inert gas
IV amine reservoir and optional mixing with inert gas
V mixing unit for phosgene-containing and amine-containing stream
VI reaction chamber
VII workup stage (quench)
VIII purification stage
IX phosgene-hydrogen chloride separation
X absorption to remove scrubbing medium (optional)
1 hydrogen chloride (HCl) feed
2 chlorine ($Cl_2$) feed 3 carbon monoxide feed
4 phosgene (fresh) feed
5 phosgene (recycled) feed
6 inert medium feed
7 amine feed
8 inert medium feed
9 amine-containing stream
10 phosgene-containing stream
11 reaction mixture
12 quench liquid
13 gaseous top discharge of quench
14 laden scrubbing liquid
15 gaseous vapors
16 scrubbing liquid
17 isocyanate (crude)
18 combined gaseous streams
19 phosgene (recycled)
20 hydrogen chloride recycling In the amine reservoir (IV), the amine 7, if appropriate together with an inert medium 8 as a carrier gas, for example nitrogen, is converted to the gas phase and fed into the mixing unit (V). Gaseous phosgene 4 is likewise obtained directly or indirectly from the phosgene production (II), optionally mixed with an inert medium 6 in stage (III) and conducted into the mixing unit (V). After the mixing in the mixing unit (V), which may consist, for example, of a nozzle or a static mixer, the gaseous mixture of phosgene, amine and if appropriate inert medium is transferred into the reaction zone (VI). As illustrated in FIG. 1, the mixing unit need not be an independent reaction stage; instead, it may be advantageous to integrate the mixing unit into the reaction zone (VI).

After the reaction in the reaction zone, the reaction mixture 11 passes into the workup stage (VII). This is preferably a so-called scrubbing tower, where the isocyanate formed is removed from the gaseous mixture by condensation in an inert solvent 12, while excess phosgene, hydrogen chloride and, if appropriate, the inert medium pass through the workup stage in gaseous form and are removed at the top as stream 13. Suitable inert solvents are preferably aromatic hydrocarbons which are optionally substituted by halogen atoms, for example chlorobenzene or dichlorobenzene, xylene and toluene. Particular preference is given to keeping the temperature of the inert solvent above the dissolution temperature of the carbamoyl chloride corresponding to the amine in the selected quench medium.

In the subsequent purification stage (VIII), the isocyanate 17 is removed from the solvent 16, preferably by rectification. It is likewise also possible here to remove residual impurities, for example hydrogen chloride, inert medium and/or phosgene (stream 15).

In general, the crude isocyanate 17 thus obtained is purified even further in a subsequent purification (not shown in FIG. 1), preferably a distillation, such that the desired purity of, for example, at least 98% by weight, preferably at least 99% by weight, more preferably at least 99.5% by weight and most preferably at least 99.8% by weight is obtained.

The solvent 16 obtained in the purification stage (VIII) can generally be recycled into the workup stage (VII) without further purification (stream 12). If required, this substream may, however, also be purified, preferably by distillation.

At least one phosgene-containing substream 13 or 15 which stems from the purification stage VIII and/or the workup stage VII, preferably these combined substreams 18, are freed at least partly of hydrogen chloride present therein in a stage (IX), and phosgene is recycled into the reaction as stream 19. To this end, it is conducted into the mixing device (V) combined with the fresh phosgene stream 4 or with the phosgene stream to the mixing device (V), or separately.

Preference is given to mixing phosgene recycle stream 19 and fresh phosgene stream 4 with one another in such a ratio that the stoichiometry desired in the reaction is attained.

The hydrogen chloride can be removed in stage (IX) by distillation and/or by means of scrubbing. When the separation is effected by means of scrubbing and a solvent is simultaneously used in the process to scrub the isocyanate out at the end of the reaction zone in stage (VII), the scrubbing medium used to separate the hydrogen chloride/phosgene mixture is preferably the same solvent as used to scrub out the isocyanate.

Figure 2:
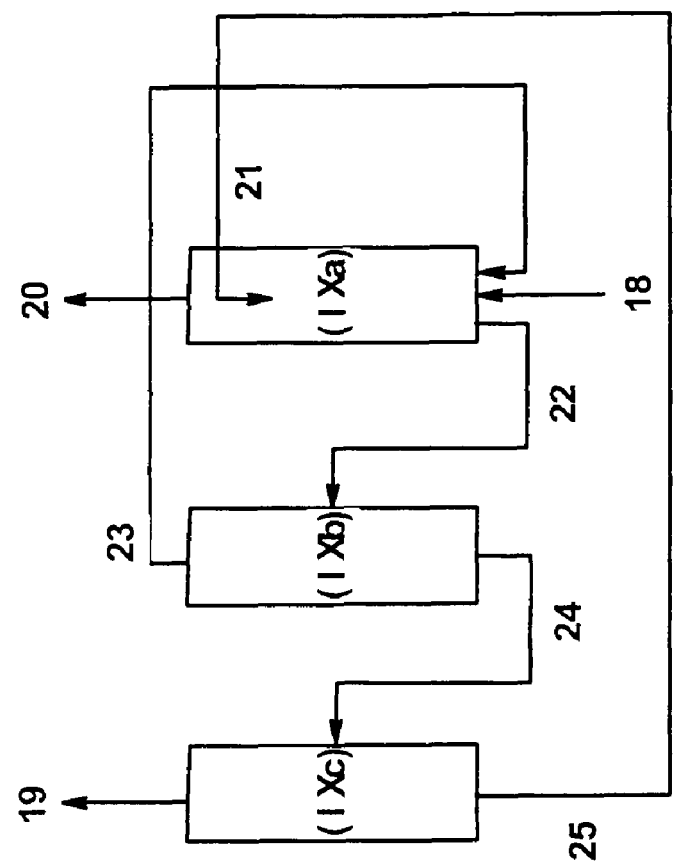
FIG. 2. A schematic diagram of a preferred embodiment of stage (IX).

A preferred embodiment of stage (IX) is shown in FIG. 2. In this figure,
(IXa) absorption for phosgene removal
(IXb) desorption or distillation to remove hydrogen chloride
(IXc) desorption or distillation to remove phosgene and scrubbing liquid
18 combined gaseous streams
19 phosgene (recycled)
20 hydrogen chloride recycling
21 scrubbing liquid
22 scrubbing liquid laden with phosgene and possibly hydrogen chloride
23 gaseous draw composed of hydrogen chloride and possibly phosgene
24 hydrogen chloride-depleted, phosgene-laden scrubbing liquid
25 scrubbing liquid (recycled)

The combined gaseous streams 18 comprising essentially phosgene and hydrogen chloride and possibly solvent from stages (VII) and/or (VIII) are contacted with scrubbing liquid 21 at a pressure of preferably from 1 to 5 bar in a scrubbing apparatus (IXa). The temperature of the scrubbing liquid is generally less than 10° C., preferably less than 0° C. and more preferably less than −5° C. The amount of scrubbing liquid is from 0.1 to 5 times the mass of the stream 18 fed in.

The scrubbing liquid may be toluene, benzene, nitrobenzene, anisole, chlorobenzene, dichlorobenzene (ortho or para or isomer mixtures thereof), trichlorobenzene, xylene, hexane, diethyl isophthalate (DEIP), tetrahydrofuran (THF), dimethylformamide (DMF) and mixtures thereof, preferably monochlorobenzene. The scrubbing liquid used is more preferably the same solvent as in stage (VII).

The scrubbing can be effected in cocurrent or preferably in countercurrent.

The scrubbing liquid 22 laden with phosgene and possibly hydrogen chloride is then conducted into a process unit (IXb), which may be a desorption or preferably a distillation to remove hydrogen chloride from this laden scrubbing liquid. When the fresh phosgene (stream 5a) comprises significant amounts of chlorine ($Cl_2$), the fresh phosgene may likewise be fed into stage (IXb) in order to achieve removal of the molecular chlorine. The pressure in the process unit is generally 0.5-5 bar above that in stage (IXa).

The separating conditions are preferably selected such that the bottoms 24 consist essentially only of phosgene and scrubbing liquid. The vapor 23 consists, in contrast, essentially of hydrogen chloride with small amounts of phosgene and scrubbing liquid, and is recycled into stage (IXa). The pressure in this unit corresponds to that in stage (IXb).

The hydrogen chloride-depleted, phosgene-laden scrubbing liquid 24 is then conducted into a desorption or preferably distillation to separate phosgene and scrubbing liquid (IXc), in which the vapor stream 19 consisting essentially of phosgene is recycled into the phosgenation, whereas the scrubbing liquid 25 which may possibly also comprise minor amounts of phosgene is recycled into the absorption (IXa). To remove chlorine traces from the fresh phosgene (stream 4a), it can likewise be fed into the dividing wall column.

Figure 3:
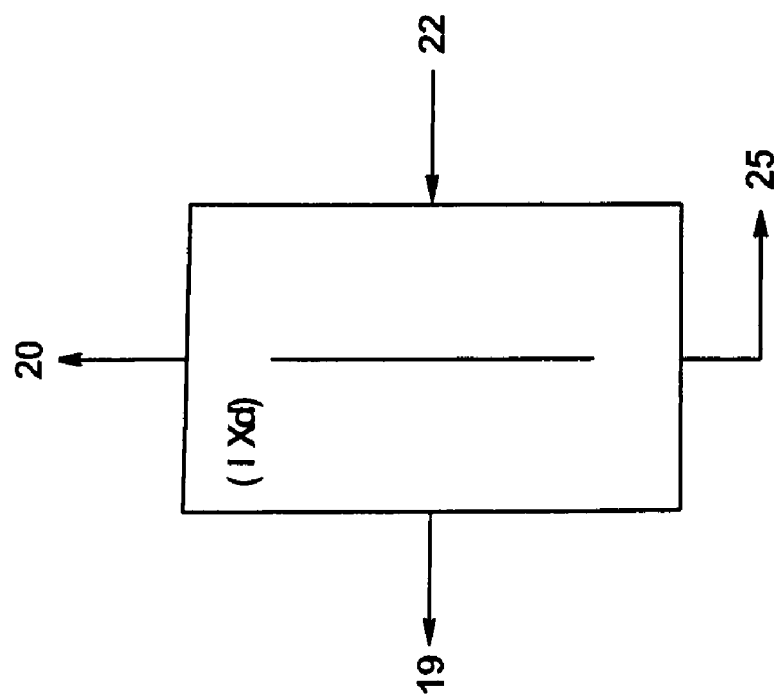
FIG. 3. A schematic diagram of a preferred embodiment of (IXd).

In a particularly preferred embodiment which is shown in FIG. 3, stages (IXb) and (IXc) are combined to a single stage (IXd); this is preferably a dividing wall distillation, in which the scrubbing liquid 22 laden with phosgene and possibly hydrogen chloride is conducted into the column from the right, such that hydrogen chloride can be removed as vapor 20 via the rectifying section, and the hydrogen chloride-depleted, phosgene-laden scrubbing liquid is separated into the components in the stripping section.

From the left-hand chamber, gaseous phosgene is then drawn off in the side draw 19, and is separated from the scrubbing liquid drawn off from the bottom 25 by means of the stripping section of the left-hand chamber and is separated from the hydrogen chloride vapor 20 by means of the rectifying section of the left-hand chamber.

The hydrogen chloride stream 20 removed in the process according to the invention may comprise further low-boiling components, especially molecular chlorine ($Cl_2$) and gaseous inerts, for example nitrogen or carbon monoxide, but also entrained scrubbing liquid from stage (IX). The dividing wall column is generally operated at a pressure of 0.5-5 bar above that in the scrubbing unit (IXa).

If desired, traces of phosgene and/or preferably scrubbing liquid can be removed in a downstream purification stage (X), for example a bed of activated carbon.

In this downstream purification stage, any impurities can be removed by absorption, adsorption, distillation or extraction. For purification, the hydrogen chloride stream can also be absorbed in water or dilute hydrochloric acid and desorbed again in a further step after removal of volatile constituents. Solvent residues can also be removed by catalytic combustion in the hydrogen chloride stream. The hydrogen chloride stream which may have been purified in this way is fed to the catalytic hydrogen chloride oxidation.

In one embodiment of the process, the stream comprising hydrogen chloride is purified by being passed over a purification bed and absorption of solvent residues present therein on the purification bed.

The purification bed consists of suitable absorbents, preferably in piece form, such as spheres, extrudates or tablets. Suitable materials useful as absorbents include, for example, activated carbon, aluminum oxide, titanium oxide, silicon dioxide, iron oxide, zeolites and molecular sieves. Suitable materials may also comprise metal oxides or metal halides, such as copper oxides or halides or ruthenium oxides or halides, or mixtures thereof, on a support composed of a refractory inorganic material such as aluminum oxide, titanium oxide or silicon dioxide.

Preferred absorbents are aluminum oxide, activated carbon and aluminas.

In a further embodiment of the process according to the invention, the stream comprising hydrogen chloride is purified by catalytic combustion of the solvent residues present therein. To this end, oxygen or an oxygen-comprising gas stream, for example air, oxygen-enriched air, technical-grade or pure oxygen, is added to the stream comprising hydrogen chloride, and this stream is passed over a fixed catalyst bed composed of oxidation catalyst.

Suitable catalysts comprise, for example, aluminum oxide, magnesium oxide, iron oxide, titanium dioxide, zirconium dioxide or mixtures thereof. The catalytic combustion of the solvent residues (hydrocarbons and/or chlorohydrocarbons) over the catalysts mentioned can already bring about partial conversion of the hydrogen chloride present to chlorine.

This partial conversion may, for example, be up to 40%, preferably up to 20%, for example from approx. 5 to 20%.

The performance of the catalytic combustion as a purification stage can also be considered as the first stage of a two-stage catalytic hydrogen chloride oxidation, the first stage being carried out over the catalysts mentioned above up to a partial conversion and the second stage (here: process stage (I)) over the ruthenium-comprising catalysts described below up to full conversion, for example a conversion of at least 70%, based on the first and the second stage. The first stage, which is carried out over inexpensive, relatively insensitive catalysts brings about an oxidation of the solvent traces which lead to coke deposits to give carbon dioxide. As a result, the expensive ruthenium catalyst used in the second stage is protected from coke-forming impurities.

It is essential to the invention that, in the process according to the invention, the phosgene present in the process stages of the actual gas phase phosgenation, i.e. process stages (III) to (IX), is present essentially in gaseous form. Only in two process stages, specifically in the quench liquid discharged from stage (VII) to stage (VIII) and in stage (IX), can phosgene be present in condensed form.

By virtue of this measure, the energy demand for the evaporation of the phosgene can be reduced compared to the gas phase phosgenation processes from the prior art.

In addition, the quotient of the amount of free phosgene present in process stages (III) to (IX) and the mass flow of isocyanate formed (stream 17) is, in accordance with the invention, less than 5 h, preferably less than 4 h, more preferably less than 3.5 h and most preferably not more than 3 h.

This causes a lowering of the holdup of phosgene in the process stages of the process according to the invention compared to the gas phase phosgenation processes from the prior art.

The amount of phosgene present in the process stages refers to all amounts of free, i.e. unreacted, phosgene which are already present in process stages (III) to (IX), i.e. the phosgene present in the individual stages and that present in the lines from one stage to another, including the recycled phosgene in line 19 (=5).

The present application further provides an integrated process for preparing diisocyanates, which comprises, as well as the above-described stages (III) to (IX) and optionally (X), also a stage (I) in which the hydrogen chloride 20 formed as a coproduct in the gas phase phosgenation process, if appropriate after passing through stage (X) (stream 1), is converted to molecular chlorine ($Cl_2$) 2, and a phosgene preparation (II) in which the molecular chlorine 2 thus formed is converted to phosgene with carbon monoxide 3.

The chlorine preparation (I) may, for example, be an electrolysis or preferably a Deacon process.

In the Deacon process, the hydrogen chloride removed is oxidized catalytically with oxygen to give chlorine.

To this end, the hydrogen chloride stream optionally purified in a stage (X), if appropriate a further stream comprising hydrogen chloride and a stream comprising oxygen are fed into an oxidation zone, and hydrogen chloride is oxidized partly to chlorine in the presence of a catalyst to obtain a product gas stream which comprises chlorine, unconverted oxygen, unconverted hydrogen chloride and steam.

In this catalytic process, also known as the Deacon process, hydrogen chloride is oxidized with oxygen in an exothermic equilibrium reaction to give chlorine, which affords steam.

Typical reaction temperatures are between 150 and 500° C.; typical reaction pressures are between 1 and 25 bar.

Since the reaction is an equilibrium reaction, it is appropriate to work at temperatures as low as possible, at which the catalyst still has a sufficient activity. Moreover, it is appropriate to use oxygen in superstoichiometric amounts. For example, a from two- to fourfold oxygen excess is typical. Since there is no risk of losses of selectivity, it may be economically advantageous to work at relatively high pressures and correspondingly at longer residence times compared to standard pressure.

Suitable catalysts comprise ruthenium oxide, ruthenium chloride or other ruthenium compounds on silicon dioxide, aluminum oxide, titanium dioxide or zirconium dioxide as supports. Suitable catalysts may, for example, be obtained by applying ruthenium chloride to the support and subsequently drying, or drying and calcining. Suitable catalysts may, in addition to or in place of a ruthenium compound, also comprise compounds of other noble metals, for example gold, palladium, platinum, osmium, iridium, silver, copper or rhenium. Suitable catalysts may also comprise chromium(III) oxide.

Typical reaction apparatus in which the catalytic hydrogen chloride oxidation is performed is a fixed bed reactor or fluidized bed reactor. The hydrogen chloride oxidation can be carried out in several stages.

The catalytic hydrogen chloride oxidation can be performed adiabatically or preferably isothermally or approximately isothermally, batchwise, preferably continuously, as a moving bed or fixed bed process, preferably as a fixed bed process, more preferably in tube bundle reactors over heterogeneous catalysts at reactor temperatures of from 180 to 500° C., preferably from 200 to 400° C., more preferably from 220 to 350° C., and a pressure of from 1 to 25 bar, preferably from 1.2 to 20 bar, more preferably from 1.5 to 17 bar and especially from 2.0 to 15 bar.

In isothermal or approximately isothermal mode, it is also possible to use a plurality of, i.e. from 2 to 10, preferably from 2 to 6, more preferably from 2 to 5, especially from 2 to 3, series-connected reactors with additional intermediate cooling.

The oxygen can be added either completely together with the hydrogen chloride upstream of the first reactor or distributed over the different reactors. This series connection of individual reactors can also be combined in one apparatus.

A preferred embodiment consists in using a structured catalyst bed in which the catalyst activity rises in flow direction. Such a structuring of the catalyst bed can be effected by means of different impregnation of the catalyst supports with active composition or by means of different dilution of the catalyst with an inert material. The inert material used may, for example, be rings, cylinders or spheres of titanium dioxide, zirconium dioxide or mixtures thereof, aluminum oxide, steatite, ceramic, glass, graphite or stainless steel. In the case of the preferred use of shaped catalyst bodies, the inert material should preferably have similar external dimensions.

Suitable shaped catalyst bodies are any shapes; preference is given to tablets, rings, cylinders, stars, wagonwheels or spheres; particular preference is given to rings, cylinders or star extrudates.

Suitable heterogeneous catalysts are especially ruthenium compounds or copper compounds on support materials which may also be doped; preference is given to optionally doped ruthenium catalysts. Suitable support materials are, for example, silicon dioxide, graphite, titanium dioxide with rutile or anatase structure, zirconium dioxide, aluminum oxide or mixtures thereof, preferably titanium dioxide, zirconium dioxide, aluminum oxide or mixtures thereof, more preferably γ- or δ-aluminum oxide or mixtures thereof.

The supported copper or ruthenium catalysts may, for example, be obtained by impregnating the support material with aqueous solutions of $CuCl_2$ or $RuCl_3$ and if appropriate of a promoter for doping, preferably in the form of its chlorides. The catalyst can be shaped after or preferably before the impregnation of the support material.

Suitable promoters for doping are alkali metals such as lithium, sodium, potassium, rubidium and cesium, preferably lithium, sodium and potassium, more preferably potassium, alkaline earth metals such as magnesium, calcium, strontium and barium, preferably magnesium and calcium, more preferably magnesium, rare earth metals such as scandium, yttrium, lanthanum, cerium, praseodymium and neodymium, preferably scandium, yttrium, lanthanum and cerium, more preferably lanthanum and cerium, or mixtures thereof.

The shaped bodies can subsequently be dried and if appropriate calcined at temperatures of from 100 to 400° C., preferably from 100 to 300° C., for example under a nitrogen, argon or air atmosphere. Preference is given to first drying the shaped bodies at from 100 to 150° C. and then to calcining them at from 200 to 400° C.

The conversion of hydrogen chloride in single pass can be restricted to from 15 to 90%, preferably from 40 to 85%, more preferably from 50 to 70%. Unconverted hydrogen chloride can, after removal, be recycled partly or fully into the catalytic hydrogen chloride oxidation. The volume ratio of hydrogen chloride to oxygen at the reactor inlet is generally between 1:1 and 20:1, preferably between 2:1 and 8:1, more preferably between 2:1 and 5:1.

Compared to the generation of chlorine by hydrogen chloride electrolysis, the catalytic hydrogen chloride oxidation has the advantage that no expensive electrical energy is required, that no hydrogen, which is critical from a safety point of view, is obtained as a coproduct, and that the hydrogen chloride supplied need not be entirely pure.

The phosgene preparation (II) has already been described above.

The performance of stages (I) and (II) is not essential to the invention. What is crucial is that the proportion of condensed or liquid phosgene in the gas phase phosgenation process according to the invention is as low as possible.

Such an integrated process can, for example, be effected as described in WO 2004/014845 or WO 2004/037718.

One advantage of such an integrated process is that the hydrogen chloride obtained as a coproduct to the diisocyanate can be utilized completely.

EXAMPLES

Example 1

Comparative

A process for preparing TDI (tolylene 2,4- and 2,6-diisocyanate isomer mixture) in the gas phase is simulated. In the production plant consisting of the stages of reaction (including reactant evaporation and superheating, reaction and quench), low boiler removal, solvent removal (monochlorobenzene, MCB) and HCl/phosgene separation, phosgene is reacted with TDA (2,4- and 2,6-tolylenediamine isomer mixture) in a molar ratio of 8:1 at 1.9 bar (abs), and unconverted phosgene is removed from the reaction mixture by distillation, removed from hydrogen chloride in a phosgene/HCl separation stage and, after condensation, recycled in liquid form into the reaction stage for reuse. Freshly supplied phosgene (19 t/h) is, after removal of excess carbon monoxide present therein by condensation, added to the recycled phosgene. The two steams are combined in a vessel cooled to −5° C. with a capacity of 30 m³ (about 21 t of phosgene at fill level 50%). The phosgene fed to the reaction stage is evaporated, heated to 350° C. in a superheater and mixed with the amine in a mixing nozzle, and then reacted. For the evaporation of the condensed phosgene stream, 6.2 MW are required.

Example 2

The system described in Example 1 is altered in accordance with the invention in such a way that both the freshly supplied phosgene and the recycled phosgene are fed in gaseous form to the superheater without preceding intermediate condensation: to this end, the recycled phosgene is withdrawn in gaseous form from the phosgene/HCl separation stage. Phosgene supplied freshly in gaseous form from the synthesis stage is added to this stream. Subsequently, the now combined phosgene stream is superheated and then fed to the reaction stage. In contrast to the procedure described in Example 1, apparatuses for condensation and the intermediate vessel are omitted; it is possible to dispense with the costly and inconvenient cooling of the intermediate vessel. The energy costs for the condensation and the evaporation of the phosgene do not arise. In addition, the total phosgene contents of the plant are reduced by the holdup of the intermediate vessel and by the condensate in the pipelines and heat exchangers. The energy demand required in Example 1 for condensation and evaporation of the phosgene does not arise.

The invention claimed is:

1. A process for preparing a diisocyanate by reacting the corresponding diamine with phosgene in a stoichiometric excess of phosgene in at least one reaction zone, comprising:
   mixing at least one stream comprising gaseous phosgene with at least one stream comprising gaseous diamine, and converting this mixture at a temperature of from 200 to 600° C. in the at least one reaction zone,
   mixing the resulting reaction mixture, which consists essentially of isocyanate, phosgene and hydrogen chloride, with at least one liquid while lowering the temperature to from 100 to 200° C., such that the isocyanate present in the reaction mixture is transferred at least partly to the liquid by condensation, while phosgene and hydrogen chloride remain in the gas phase,
   working up the condensed isocyanate with evaporation of the phosgene and hydrogen chloride present in the condensed phase,
   separating the combined gaseous streams comprising essentially hydrogen chloride and phosgene into a stream comprising predominantly phosgene and a stream comprising predominantly hydrogen chloride,
   recycling the thus obtained stream comprising predominantly phosgene into the mixing,
   wherein the phosgene present in the process stages is present essentially in gaseous form.

2. The process according to claim 1, wherein the diisocyanate is a (cyclo)aliphatic diisocyanate.

3. The process according to claim 1, wherein the diisocyanate is selected from the group consisting of 1,6-diisocyanatohexane, 1-isocyanato-3,3,5-trimethyl-5-(isocyanatomethyl)cyclohexane and 4,4'-di(isocyanatocyclohexyl)methane.

4. The process according to claim 1, wherein the diisocyanate is an aromatic diisocyanate.

5. The process according to claim 4, wherein the diisocyanate is at least one selected from the group consisting of monomeric methylenedi(phenyl isocyanate) (MDI), tolylene 2,6-diisocyanate, tolylene 2,4-diisocyanate (TDI) and naphthyl diisocyanate (NDI).

6. The process according to claim 1, wherein the isocyanate is phenyl isocyanate.

7. The process according to claim 1, wherein the phosgene conducted into said mixing comprises carbon monoxide.

8. The process according to claim 1, wherein the fresh phosgene conducted into the process stages comprises molecular chlorine.

9. The process according to claim 8, wherein the phosgene comprising molecular chlorine, before being fed into the reaction zone, first passes through said separating.

10. The process according to claim 1, wherein the molar ratio of phosgene to amino groups in the reaction zone is from 1.1:1 to 20:1.

11. The process according to claim 1, wherein said working up is operated at a pressure of from 0.1 to 20 bar and a temperature of from 100 to 200° C.

12. The process according to claim 1, wherein said separating is operated such that the mass fraction of hydrogen chloride in the phosgene-containing stream, after optional mixing with fresh phosgene before the mixing with the amine-containing stream, is less than 15% by weight.

13. The process according to claim 1, wherein the quotient of the amount of free phosgene present in said working up and separating and the mass flow of isocyanate formed is less than 5 h.

* * * * *